United States Patent [19]

Sano et al.

[11] Patent Number: 4,980,285

[45] Date of Patent: Dec. 25, 1990

[54] METHOD FOR PRODUCING L-AMINO ACIDS

[75] Inventors: Konosuke Sano, Tokyo; Chieko Osumi; Kazuhiko Matsui, both of Kawasaki; Kiyoshi Miwa, Matsudo, all of Japan

[73] Assignee: Ajinomoto Co., Inc., Tokyo, Japan

[21] Appl. No.: 412,562

[22] Filed: Sep. 25, 1989

Related U.S. Application Data

[63] Continuation of Ser. No. 784,467, Oct. 4, 1985, abandoned.

[30] Foreign Application Priority Data

Oct. 4, 1984 [JP] Japan ................... 59-208677

[51] Int. Cl.$^5$ .................... C12N 15/52; C12N 1/21; C12N 15/74; C12P 13/08; C12P 13/22
[52] U.S. Cl. ................... 435/108; 435/69.1; 435/71.1; 435/170; 435/172.1; 435/172.3; 435/115; 435/252.3; 435/252.32; 435/320; 435/840; 536/27; 935/6; 935/9; 935/22; 935/29; 935/59; 935/60; 935/61; 935/66; 935/72

[58] Field of Search ........... 435/252.3, 252.33, 252.32, 435/108, 115, 69.1, 71.1, 170, 172.1, 172.3, 320, 840; 935/23, 27, 29, 38, 6, 9, 22, 59, 60, 61, 66, 72; 536/27

[56] References Cited

U.S. PATENT DOCUMENTS

| 4,371,614 | 3/1983 | Anderson et al. | 435/108 |
| 4,500,640 | 3/1985 | Katsumata et al. | 435/253 |
| 4,757,009 | 7/1988 | Sano et al. | 435/106 |

*Primary Examiner*—Richard A. Schwartz
*Assistant Examiner*—Richard C. Peet
*Attorney, Agent, or Firm*—Oblon, Spivak, McClelland, Maier & Neustadt

[57] ABSTRACT

A method for producing an L-amino acid, which comprises inserting a gene which codes for an enzyme which is utilized on the route of biosynthesis of an L-amino acid product into one of at least two plasmid vectors which have compatible replicating origins different from each other, inserting a second gene which codes for an enzyme different from the first enzyme on the route of biosynthesis of the L-amino acid into a second of the plasmid vectors; introducing the thus obtained recombinant plasmids into a strain of Coryneform bacteria; and culturing the thus transformed strain which is capable of producing the L-amino acid, said two enzymes being highly rate determining enzymes for the biosynthesis of L-amino acid.

3 Claims, No Drawings

METHOD FOR PRODUCING L-AMINO ACIDS

This application is a continuation of application Ser. No. 06/784,467, filed on Oct. 4, 1985, now abandoned.

BACKGROUND OF THE INVENTION

1. Field of the Invention

The present invention relates to a method for producing L-amino acids. More particularly, the present invention relates to a method for producing L-amino acids by fermentation using Coryneform bacteria grown by a recombinant DNA technique.

2. Description of the Background

Many examples of culturing amino acid-producing bacteria by recombinant DNA techniques are already known. In all of these methods, microorganisms, which carry a recombinant plasmid obtained by inserting a gene coded for one or more enzymes on one kind of plasmid vector, are employed. However, the high productivity of product amino acid is not always achieved, and a need still continues to exist for a method of producing amino acids in high yields using recombinant DNA technology.

SUMMARY OF THE INVENTION

Accordingly, one object of the present invention is to provide a method of culturing Coryneform bacteria utilizing recombinant DNA methodology in order to achieve improved yields of L-amino acids.

Briefly, this object and other objects of the present invention as hereinafter will become more readily apparent can be attained by a method for producing an L-amino acid by inserting a gene which codes for an enzyme which is utilized on the route of biosynthesis of an L-amino acid product into one of at least two plasmid vectors which have compatible replicating origins different from each other; inserting a second gene which codes for an enzyme different from said first enzyme on the route of biosynthesis of said L-amino acid into a second of said plasmid vectors; introducing the thus obtained recombinant plasmids into a strain of Coryneform bacteria; and culturing the thus transformed strain which is capable of producing the said L-amino acid, said two enzymes being highly rate determining enzymes for the biosynthesis of said L-amino acid.

DETAILED DESCRIPTION OF THE PREFERRED EMBODIMENTS

In the present invention, two or more plasmid vectors are incorporated, as described above, into a strain of *Coryneform* bacteria. This means of course, that at least two plasmid vectors are used. However, three or four plasmid vectors may incorporated in the strain of Coryneform bacteria. However, the incorporation of too many plasmid vectors into an organism can cause technical difficulties.

In the present invention, it is necessary that two or more plasmids be present in a microorganism. It has been found in the research leading to the present invention, however, that the two kinds of plasmids which originate from e.g., plasmid pAM 330, which is carried by *Brevibacterium lactofermentum*, can only be incorporated in a strain of Coryneform bacterium with great difficulty. Accordingly, it has been found that it is necessary for the plasmids which are incorporated in a microorganism to have different replicating origins in order for the plasmids to be both present in the microorganism. For both plasmids to be present, it is sufficient that the replicating origins are compatible, but other sites can be identical. In order to test if plasmids can both be present in a microorganism, a determination must be made if chemical resistance is exhibited by two or more plasmids. The term replicating origin is used to refer to a DNA region in which replication of plasmid DNA is totally coded.

The phrase "enzyme on the route for biosynthesis of a certain amino acid" refers to the situation in which, for example, when glucose is used as a carbon source for the production of threonine, a series of enzymes governs the route for biosynthesis starting from glucose to phosphoenol pyruvate and then to pyruvate and also a series of enzymes governs the biosynthesis process starting from phosphoenol pyruvate to oxaloacetate and then to aspartate. A still further process governs the route from pyruvate to oxaloacetate and then to aspartate via acetyl CoA through the TCA cycle. Yet another process governs the route from aspartate to threonine via homoserine.

In the case of the production of tryptophan, when glucose is used as a carbon source, a series of enzymes governs the biosynthesis from glucose to phosphoenol pyruvate, another group of enzymes governs biosynthesis starting from phosphoenol pyruvate to chorismate. Still another route goes from anthranilate to tryptophan. In the case of proline, enzymes govern the route of biosynthesis from glucose to phosphoenol pyruvate and pyruvate, while other enzymes govern the route starting from phosphoenol pyruvate and entering into the TCA cycle via oxaloacetate. Other enzymes govern the route starting from pyruvate and entering into the TCA cycle via acetyl CoA. Still other enzymes govern the route starting from the TCA cycle and reach proline via glutamate. In the case of phenylalanine, a series of enzymes governs the route starting from glucose to phosphoenol pyruvate. Other enzymes govern the route from chorismate to phenylalanine via prephenate. In the case of valine, a series of enzymes governs the route starting from glucose and reaching pyruvate and threonine, while other enzymes govern the route to valine via α-acetolactate.

In order to ascertain if a given enzyme is highly rate-determining, a product of a certain enzyme is added in vivo or in vitro to the reaction system. If an increase in the rate of biosynthesis of a given final, objective amino acid is observed, the enzyme is rate-determining. Further, other highly rate-determining enzymes can be determined in a similar manner. The enzymes which are to be used are inserted in the order of their rate-determining abilities, but this is not always necessary.

Suitable examples of genes on enzymes and amino acids ar shown below. For the production of threonine by fermentation, aspartate kinase (2.7.2.4), phosphoenol pyruvate carboxylase (6.4.1.1), homoserine dehydrogenase (1.1.1.3), homoserine kinase (2.7.1.39), threonine synthase (4.2.99.2), aspartate aminotransferase (2.6.1.1), and the like are employed.

For the production of lysine by fermentation, aspartate kinase, phosphoenol pyruvate carboxylase, aspartate aminotransferase, aspartate semialdehyde dehydrogenase (1.2.1.11), dehydropicolinate synthase (4.2.1.52), dihydropicolinate reductase (1.3.1.26), succinyl-diaminopimelate aminotransferase (2.6.1.17), succinyl-L-diaminopimelate desuccinylase (3.5.1.18), diaminopimelate epimerase (5.1.1.7), diaminopimelate decarboxylase (4.1.1.20), and the like are employed.

For the production of tryptophan, by fermentation, not only can biosynthesis enzymes up to phosphoenol pyruvate be employed, but also 3-deoxy-D-arabinoheptulonate 7-phosphate synthase, 3-dehydroquinate synthase (4.2.1.10), shikimate dehydrogenase (1.1.1.25), shikimate kinase (2.7.1.71), 5-enolpyruvylshikimate synthase (2.5.1.19), chorismate synthase, anthranilate synthase (4.1.3.27), anthranilate phosphoribosyl transferase, N-(5'-phosphoribosyl)anthranilate isomerase, indole-3-glycerol-phosphate synthase (4.1.1.48) and tryptophan synthase (4.2.1.20).

For the production of phenylalanine by fermentation, enzymes similar to those used for the production of tryptophan can be employed, and in addition, the enzymes from deoxy-arabino-heptulosonate phosphate synthase to chorismate synthase, chorismate mutase and prephenate dehydratase (4.2.1.51).

The Coryneform bacteria, which are used in the present invention, are the aerobic, gram-positive, nonacid fast rods described in Bergey's Manual of Determinative Bacteriology, 8th edition, page 599 (1974). Among these strains, the *Coryneform* bacteria which produce L-glutamic acid in large quantities are described as follows:

Brevibacterium divaricatum ATCC 14020
Brevibacterium saccarolyticum ATCC 14066
Brevibacterium immariophilum ATCC 14068
Brevibacterium lactofermentum ATCC 13869
Brevibacterium roseum ATCC 13825
Brevibacterium flavum ATCC 13826
Brevibacterium thiogenitalis ATCC 19240
Corynebacterium acetoacidophilum ATCC 13870
Corynebacterium acetoglutamicum ATCC 15806
Corynebacterium callunae ATCC 15991
Corynebacterium glutamicum ATCC 13032, 13060
Corynebacterium lilium ATCC 15990
Corynebacterium melassecola ATCC 17965
Corynebacterium ammoniaphilum ATCC 15354

In addition to the above-mentioned glutamic acid-producing Coryneform bacteria, the glutamic acid-producing Coryneform bacteria of the present invention include variants which produce amino acids such as lysine, arginine, and the like.

In order to isolate the genes which participate in the biosynthesis of amino acids, chromosomal genes are first extracted, for example, by the method described by H. Saito and K. Miura, in *Biochem. Biophys. Acta,* 72, 619 (1963), from strains which carry the genes which take part in the biosynthesis of amino acids, and then the extracted genes are digested with an appropriate restriction enzyme. The digested chromosomal genes are ligated with plasmid vectors which are capable of propagating in Coryneform bacteria. Using the resulting recombinant DNAs, amino acid-auxotrophic variants of Coryneform bacteria are transformed and, strains which have lost auxotrophy for amino acids are isolated. (This is the most convenient method to isolate the objective gene clone. However, the other methods such as the chromosomal gene walking method and the fishing method which use isotope-labeled reassembled DNA fragments may also be used.) From the strains, the genes which participate in the biosynthesis of amino acids can be isolated.

In order to cleave the chromosomal genes, a wide variety of restriction enzymes can be employed, if the degree of cleavage can be controlled by controlling the time for the cleavage reation, and other factors.

The plasmid vector used in the present invention can be any vector, as long as it can be propagated in cells of Coryneform bacteria. Specific examples include the following:

(1) pAM 330 cf. Published Unexamined Japanese Patent Application No. 67699/83
(2) pAM 1519 cf. Published Unexamined Japanese Patent Application No. 77895/83)
(3) pAJ 655 cf. Published Unexamined Japanese Patent Application No. 216199/83
(4) pAJ 611 cf. Published Unexamined Japanese Patent Application No. 216199/83
(5) pAJ 1844 cf. Published Unexamined Japanese Patent Application No. 216199/83

Other examples of plasmids which are capable of propagating in Coryneform bacterial cells include pCG 1 (Published Unexamined Japanese Patent Application 134500/82), pCG 2 (Published Unexamined Japanese Patent Application 35197/83) and, pCG 4 and pCG 11 (Published Unexamined Japanese Patent Application 183799/82), pCC 1 (Published Unexamined Japanese Patent Application 143591/84) and pBL 100 (Published Unexamined Japanese Patent Application 120992/85).

When two or more plasmids selected from amongst these plasmids are employed, the object of the present invention can be achieved. The vector DNA is cleaved by the same restriction enzyme which is used to cleave the chromosomal gene, or the vector DNA is connected with an oligonucleotide which has a complementary base sequence at its respective terminals for the chromosomal DNA cleavage fragment and the cleaved vector DNA. Then, the resulting composite is subjected to a ligation reaction to join the plasmid vector and the chromosomal fragment.

The incorporation of the thus obtained recombinant DNA of the chromosomal DNA and the vector plasmid into recipients belonging to *Coryneform* bacteria can be achieved by any one of several methods. One method comprises treating the recipient cells with calcium chloride to increase the permeability of DNA, as is reported regarding *Escherichia coli* K-12 (Mandel, M. and Higa, A., *J. Mol. Biol.*, 53, 159 (1970). Another method comprises incorporating the recombinant DNA at a stage of growth (the so-called competent cell) when cells become capable of incorporating DNA therein, as is reported for *Bacillus subtilis* (Ducan, C. H., Wilson, G. A. and Young, F. E., *Gene,* 1, 153 (1977)). Alternatively, it is also possible to incorporate the plasmids into the DNA recipients by forming protoplasts or spheroplasts of the DNA recipients, which easily incorporate plasmid DNA, as is known for *Bacillus subtilis*, Actinomycetes and yeast (Chang, S. and Cohen, S. N., *Molec. Gen. Genet.,* 168, 111 (1979); Bibb, M. J., Ward, J. M. and Hopwood, O. A., *Nature,* 274, 398 (1978); Hinnen, A., Hicks, J. B. and Fink, G. R., *Proc. Natl. Acad. Sci. USA,* 75, 1929 (1978)).

In the protoplast technique, a sufficiently high frequency can be achieved even by the above-described process which is used for *Bacillus subtilis*. Another process comprises allowing DNAs to incorporate into protoplasts of the genus Corynebacterium or the genus Brevibacterium, as described in Published Unexamined Japanese Patent Application 183799/82, in the presence of polyethylene glycol or polyvinyl alcohol. Divalent metal ions can also be utilized, of course. By a process in which the incorporation of DNAs is accelerate by the addition of carboxymethyl cellulose, dextran, phycoll, Pluronic F 68 (Serva Co., Ltd.), or the like, in place polyethylene glycol or polyvinyl alcohol, similar results can also be achieved.

In order to obtain strains carrying recombinant DNAs which have genes ligated thereto which participate in the biosynthesis of amino acids to vector plasmids, the thus recombined DNAs are transformed using amino acid-auxotroph as a recipient and the transformants, from which amino acid-auxotrophy has been lost, may be separated. In the cases where a phenotype such as analogue resistance, or the like, is imparted by the introduction of the genes participating in biosynthesis of amino acids, transformants containing the objective recombinant DNAs can be easily obtained using its phenotype as an index in lieu of an amino acid-auxotrophic phenotype.

The recombinant DNAs, which have connected thereto the genes which participate in the biosynthesis of amino acids, can be separated from the thus obtained transformants and introduced into strains carrying recombinant DNAs, along with another gene which participates in biosynthesis of amino acids obtained in a manner similar to the above, whereby amino acid-producing strains can be effectively obtained.

To isolate the recombinant DNAs, bacteria are lysed, for example, by treatment with lysozyme and SDS, and then are treated with phenol. Two volumes of ethanol are subsequently added thereto to precipitate and recover DNAs.

In order to introduce a plurality of plasmids into a microorganism, the plasmids may be introduced one by one as described above. However, a mixture of a plurality of plasmids may also be incorporated into a microorganism.

The transformants which carry a plurality of recombinant DNAs obtained as described above often per se produce various amino acids. However, in order to obtain amino acid-producing bacteria which have a higher productivity, transformation may be achieved by recombinant DNAs using strains using a high productivity of a given amino acid. Representative examples of recipients of the recombinant DNAs include homoserine auxotrophic bacteria, S-(2-aminoethyl)-cystein-resistant bacteria, and the like, when lysineproducing bacteria are desired. For the production of arginine, 2-thiazole-alanine-resistant bacteria are used. For the production of threonine, α-amino-β-hydroxyvaleric acid-resistant bacteria are used. For the production of isoleucine, α-amino-β-hydroxyvaleric acid-resistant bacteria are used. For the production of proline, 2,4-dehydroprolic acid-resistant bacteria are used. For the production of glutamic acid, ketomaleic acid-resistant bacteria are used.

The method which is used to culture the L-amino acid-producing bacteria obtained is similar to known conventional methods for culturing L-amino acid-producing bacteria. That is, culturing can be conducted using an ordinary medium containing carbon sources, nitrogen sources and inorganic ions and, if necessary, further containing organic trace nutrients such as amino acids, vitamins, and the like. Suitable carbon sources include glucose, sucrose, lactose, and the like and starch hydrolysate containing these materials, as well as whey, molasses, and the like. Suitable nitrogen sources include ammonia gas, ammonia water, ammonium salts and so on.

Incubation is performed under aerobic conditions under appropriate pH control and proper temperature control of the medium until the production and accumulation of L-amino acids substantially ceases. By the method of the present invention substantial amounts of L-amino acids can be produced and accumulated in a culture solution. From the culture solution, the product L-amino acids can be collected by conventional methods.

Having generally described this invention, a further understanding can be obtained by reference to certain specific examples which are provided herein for purposes of illustration only and are not intended to be limiting unless otherwise specified.

EXAMPLE 1

Production of L-threonine from a plasmid combination of a plasmid carrying phosphoenol pyruvate carboxylase (PEPC) gene and a plasmid carrying homoserine dehydrogenase (HD) gene:

1-1. Cloning of PEPC gene 1-1-1. Preparation of donor DNA:

Brevibacterium lactofermentum ATCC 13869 was inoculated in 1 liter of CMG medium which contained 1 g/dl of peptone, 1 g/dl of yeast extract, 0.5 g/dl of glucose and 0.5 g/dl of NaCl and which had been adjusted to a pH of 7.2. The culture was agitated at 30° C. for about 3 hours and the cells were harvested at an exponential growth phase. After the cells were lysed by lysozyme and SDS, chromosomal DNAs were extracted and purified by the conventional phenol method, and 3.5 mg of DNA material was obtained.

1-1-2. Preparation of vector DNA:

As a vector, pAJ 43 (molecular weight, 3.4 megadaltons; harbored in Brevibacterium lactofermentum, AJ 11997, deposited as FERM-P 6857) was used. The history of pAJ 43 is described in Published Unexamined Japanese Patent Application 192900/8). pAJ 655 is the mother plasmid of pAJ 43, and pAJ 655 can be obtained from pAM 330 which is natively carried in Brevibacterium lactofermentum ATCC 13869.

pAJ 655-carrying Brevibacterium lactofermentum No. 64 (ATCC-39134) was incapable of growing on CMG agar medium which contained 10 g/dl of peptone, 10 g/dl of yeast extract, 5 g/dl of glucose, 5 g/dl of NaCl and 20 g/dl of agar and which had been adjusted to a pH of 7.2 containing 100 μg/ml of chloramphenicol. The bacteria was pre-cultured in CMG medium without chloramphenicol and then was subsequently cultured at 30° C. in CMG liquid medium containing 100 μg/ml of chloramphenicol overnight. An appropriate amount of the culture solution was spread over the CMG medium containing the same concentration of chloramphenicol. By culturing at 30° C. for 1 or 2 days, a strain having a resistance of 100 μg/ml of chloramphenicol was obtained. The chloramphenicol resistance of this strain was examined in CMG medium. The strain showed a resistance up to 200 μg/dl and was very stable.

A plasmid carried on the thus obtained strain having a resistance to high concentrations of chloramphenicol, as described above, was named pAJ 43, which DNA was prepared in the manner described below.

First, 1 liter of CMG liquid medium containing 10 μg/ml of chloramphenicol was inoculated with the above described strain. After culturing at 30° C. to reach a late exponential growth phase, the cells were collected. After the cells were lysed by lysozyme and SDS in a conventional manner, the supernatant was obtained by ultracentrifugation at 30,000×g for 30 minutes. Polyethylene glycol (final concentration, 10%) was added to the supernatant to precipitate DNA. After concentrating, the precipitate was dissolved in 10 ml of EDTA.NaCl buffer (pH 8.0). After treating the DNA with ribonuclease (reacting with 50 μg/ml of ribonuclease I at 37° C. for 30 minutes), the DNA was treated with phenol. Then 2 volumes of ethanol was added to the extract and the DNA was precipitated at −20° C. The precipitate was dissolved in 1 ml of tris.EDTA.-NaCl (TEN) buffer. The DNA solution was subjected to agarose gel electrophoresis (voltage of 5 V per 1 cm of gel, 15 minutes) to fractionate and harvest 150 μg of pure pAJ 43 plasmid DNAs as a final amount.

Properties of pAJ 43 DNAs

The molecular weight of pAJ 43 was determined by agarose gel electrophoresis performed in accordance with the method of P. A. Sharp, et al., *Biochemistry*, 12, 3055 (1973) using 0.8% gel at a constant voltage of 5 V per cm of gel length for 15 hours. The molecular weight was calculated as 53.4 Md by comparing its mobility to the mobility of molecular weight markers having known molecular weights (λ Phage Hind III fragments (purchased from BRL Co., Ltd.) after complete digestion of pAJ 43 DNA with restriction enzyme Hind III).

As a result of mapping by restriction enzymes, it was observed that pAJ 43 was generated from pAJ 655 through delection in vivo. pAJ 43 is a small size plasmid comprising about 1 Md of a fraction containing a chloramphenicol-resistant gene region of pBR 325 and about 2.4 Md of fragment containing a region essential for maintaining replication of pAM 330.

1-1-3. Insertion of chromosomal DNA fragment into vector

The chromosomal DNAs, 20 μg, obtaining in 1-1-1 and 10 μg of the plasmid DNAs obtained in 1-1-2 were each treated with restriction endonuclease Hind III at 37° C. for 1 hours to fully cleave them. After heat treatment at 65° C. for 10 minutes, both reaction solutions were mixed with each other, and the mixture was subjected to a ligation reaction between the DNA strands with T4 phase-derived DNA ligase at 10° C. for 24 hours in the presence of ATP and dithiothreitol. After heat treatment at 65° C. for 10 minutes, a 2-fold volume of ethanol was added to the reaction solution to precipitate DNA.

1-1-4. Cloning of PEPC qene

A glutamate auxotroph, *Brevibacterium lactofermentum* (AJ 12061) having a PEPC activity reduced by 50% was used as a recipient. The protoplast transformation method was used as the transformation technique. Firstly, the strain was cultured in 5 ml of CMG liquid medium until an early exponential growth phase was reached. After adding 0.6 unit/ml of penicillin G thereto, the culture was shaken for a further 1.5 hour. The cells were harvested by centrifugation and washed with 0.5 ml of SMMP medium (pH 6.5) composed of 0.5M sucrose, 20 mM maleic acid, 20 mM magnesium chloride and 3.5% Pennassay broth (Difco). Then, the cells were suspended in SMMP medium containing 10 mg/ml of lysozyme to form protoplast at 30° C. for 20 hours. After centrifugation at 6000×g for 10 minutes, the protoplasts were washed with SMMP and resuspended in 0.5 ml of SMMP. The thus obtained protoplasts were mixed with 10 μg of DNAs as prepared in reaction 1-1-3 above in the presence of 5 mM EDTA. After polyethylene glycol was added to the mixture to give a final concentration of 30%, the mixture was allowed to stand at room temperature for 2 minutes to incorporate DNAs into the protoplasts. After the protoplasts were washed with 1 ml of SMMP medium, the protoplasts were resuspended in 1 ml of SMMP and, the suspension was incubated at 30° C. for 2 hours to complete phenotypic expression. The culture solution was spread on a protoplast regeneration medium containing, per one liter of distilled water, 12 g of tris(hydroxymethyl)aminomethane, 0.5 g of KCl, 10 g of glucose, 8.1 g of $MgCl_2.6H_2O$, 2.2 g of $CaCl_2.2H_2O$, 4 g of peptone, 4 g of powdered yeast extract, 1 g of Casamino acid (Difco Co., Ltd.), 0.2 g of $K_2HPO_4$, 135 g of sodium succinate, 8 g of agar, 3 μg/ml of chloramphenicol at pH 7.0.

After culturing at 30° C. for 2 weeks, approximately 500 colonies resistant to chloramphenicol appeared, which were replicated on a glutamic acid-free medium (2% glucose, 1% ammonium sulfate, 0.3% urea, 0.1% $KH_2PO_4$, 0.04% $MgSO_4.7H_2O$, 2 ppm iron ions, 2 ppm manganese ions, 200 μg/dl thiamine hydrochloride and 50 μg/dl of biotin, pH 7.0, 1.8% agar) to obtain a strain resistant to chloramphenicol and having prototrophy for glutamic acid. This recombinant strain was named AJ 12066 and was deposited as (FERM-P 7176) or (FERM-BP 590).

1-1-5. Plasmid analysis of transformant:

From AJ 12066 (FERM BP-590), a lysate was prepared by the method described in section 1-1-2. When plasmid DNA was detected by agarose gel electrophoresis, a plasmid having a molecular weight of 10.5 Md, which was obviously larger than vector pAJ 43, was detected. The recombinant plasmid was named pAJ 200.

1-1-6. Retransformation:

In order to confirm that the PEPC gene was present on the recombinant plasmid carrying the DNA fragment of 7.1 Md detected in section 1-1-5 above, *Brevibacterium lactofermentum* AJ 12061 was transformed using pAJ 200 DNA. Among the colonies which appeared, which had chloramphenicol-resistance, 30 strains were purified and examined for their prototrophy for glutamic acid. The examination indicated all of the strains had lost their auxotrophy. It became clear that the PEPC gene was present on the recombinant plasmid pAJ 200.

1-1-7. Stabilization of pAJ 200:

The above described plasmid PAJ210 was very unstable, and an attempt was made to form stable plasmids.

During the protoplast transformation of Coryneform bacteria, a plasmid having a large molecular weight insert sometimes results in in vivo miniaturization and stabilization, because partial omission of a DNA region may occur. Investigations of plasmids were performed on 100 retransformants. As a result, miniaturized plasmids were detected in 8 strains. These miniaturized plasmids were stably maintained. From one strain of plasmid named pAJ 201, large quantities were prepared and characterized by restriction enzyme.

1-2. Cloning of Homoserine Dehydrogenase (HD) gene 1-2-1. Preparation of donor DNA carrying HD gene:

Chromosomal DNA was extracted from a α-amino-β-hydroxyvaleric acid-resistant mutant AJ 11188 (FERM-P 4190) (Published Examined Japanese Patent Application 3038/81) of *Brevibacterium lactofermentum* ATCC 13869, and was purified in the manner described in section 1-1-1 above.

1-2-2. Preparation of vector DNA:

pAJ 1844 (Published Unexamined Japanese Patent Application No. 192900/83) (molecular weight, 5.4 Md, derived from pHM 1519 which is natively harbored in *Corynebacterium glutamicum* ATCC 1519, was used as a vector and its DNA was separated as follows:

A 100 ml CMG medium containing 100 μg/ml of chloramphenicol was inoculated with *Brevibacterium lactofermentum* AJ 12037 (FERM-P 7234) (FERM-BP 577) which carries pAJ 1844 as a plasmid in the manner described in section 1-1-2 above. Approximately 80 μg of pAJ 1844 plasmid DNA was obtained.

1-2-3. Insertion of chromosomal DNA fragment into vector:

The chromosomal DNA, 40 μg, obtained in section 1-2-1, was partly digested with 0.124 units of restriction enzyme Pst I at 30° C. for 10 minutes. The plasmid DNA, 10 μg, obtained in section 1-2-2 was treated with restriction endonuclease Pst I at 37° C. for 2 hours to fully cleave the plasmid. After heat treatment at 65° C. for 10 minutes, both reaction solutions were mixed with each other, and the mixture was subjected to a ligation reaction with $T_4$ phage-derived DNA ligase at 22° C. for 15 hours in the presence of ATP and dithiothreitol. After heat treatment at 65° C. for 5 minutes, a 2-fold volume of ethanol was added to the reaction solution to precipitate and harvest DNA after completion of the ligation reaction.

1-2-4. Cloning of HD gene:

Homoserine auxotroph of *Brevibacterium lactofermentum* (AJ 12019) (NRRLB-15346) was used as a recipient. Tranformation was performed in the manner described in section 1-1-4. After culturing at 30° C. for 10 days, AJ 12020 (FERM-BP 269) resistant to chloramphenicol and having the prototrophy for homoserine was obtained.

1-2-5. Plasmid analysis of the transformant:

From AJ 12066 (FERM BP-590), a lysate was prepared by the method described in section 1-1-2. Agarose gel electrophoresis was used for plasmid detection and a plasmid having a molecular weight of 7.64 Md was detected and named pAJ 210.

1-2-6. Preparation of DNA fragment harboring kanamycin-resistant gene and insertion thereof into plasmid pAJ 201:

Plasmid pUC4K (Veriera, J. and Messing, J., *Gene*, 19:259, 1982, purchased from Pharmacia Co., Ltd.), 20 μg, was reacted with 20 units of restriction enzyme Bam H 1 at 37° C. for 2 hours to fully digest the plasmid. By subjecting the reaction mixture to agarose gel electrophoresis, approximately 1.4 kb of DNA fragments harboring kanamycin-resistant genes were separated and purified. Plasmid pAJ 201 DNA, 2 μg, obtained as described in section 1-1-7, was fully cleaved with restriction enzyme Bgl II. The material obtained was mixed with the DNA fragments of pUC4K containing kanamycin-resistant gene and was ligated. After heat treatment, ethanol was added to the ligated materials to precipitate the DNA. The obtained DNA was introduced into *Brevibacterium lactofermentum* AJ 12036 (FERM-P 7559) by the transformation method described in section 1-1-4.

After culturing at 30° C. for 2 weeks, approximately 10 colonies resistant to kanamycin appeared. From these strains, a lysate was prepared and plasmid DNAs were detected by agarose gel electrophoresis in the manner described in section 1-1-2, whereupon plasmid obviously larger than pAJ 201 was detected. The plasmid was named pAJ 201K. pAJ 201K was introduced into *Brevibacterium lactofermentum* AJ 12061. Among the produced kanamycin-resistant colonies, 25 strains were transfered on glutamic acid-free medium. All of them were resistant to kanamycin and glutamic acid prototroph. It was thus confirmed that PEPC gene and kanamycin-resistant gene were present on pAJ 201K and expressed.

1-3. Improvement of L-threonine productivity in the presence of both pAJ 201K and pAJ 210:

By the transformation method, pAJ 210 was introduced into the threonine-producing, α-amino-β-hydroxyvaleric acid-resistant mutant, *Brevibacterium lactofermentum* AJ 11188 (FERM-P 4190). The transformants were selected in terms of resistance to chloramphenicol, and the strain AJ 12021 (FERM-BP 270) was obtained. Further, the plasmid pAJ 201K (FERM-BP 270) obtained as described in section 1-2-6 was introduced into pAJ 12021, and the transformants were selected in terms of resistance to chloramphenicol and kanamycin. AJ 12167 (FERM-P 7879) was obtained which carries two kinds of plasmids: pAJ 201K and pAJ 210.

Strains AJ 11188, AJ 12021 and AJ 12167 were cultured (with shaking) at 30° C. for 72 hours in a threonine-producing medium (10 g/dl of glucose, 3 g/dl of $(NH_4)_2SO_4$, 0.1 g/dl of $KH_2PO_4$, 0.04 g/dl of $MgSO_4 \cdot 7H_2O$, 10 mg of $FeSO_4 \cdot 7H_2O$, 10 mg of $MnSO_4 \cdot 5H_2O$, 300 μg/l of thiamine.HCl, 100 μg/l of biotin, 45 gm/dl (as total nitrogen) of soybean protein acid hydrolysate ("Aji-Eki"), 25 mg/dl of isoleucine, 30 mg/dl of leucine, pH 7.0, 5 g/dl of $CaCO_3$ (separately sterilized)). After culturing, L-threonine, in the supernatant, was quantitatively determined by high speed liquid chromatography. The results are shown in Table 1.

TABLE 1

| Strain | Amount of L-Threonine Accumulated (g/dl) |
|---|---|
| AJ 11188 | 1.09 |
| AJ 12021 | 1.78 |
| AJ 12167 | 2.09 |

By the transformation method, pAJ 210 was introduced into *Corynebacterium glutamicum* ATCC 13287 having auxotrophy for homoserine, and a strain SR 8301 (NRRL B-15348) was obtained. Further, pAJ 201K was introduced thereinto and transformants were selected in terms of resistance to kanamycin and resistance to chloramphenicol. AJ 12168 (FERM-P 7880), carrying both plasmids pAJ 210 and pAJ 201K, was obtained. Production tests for threonine were carried out in the same manner as described in Table 1. The results are shown in Table 2.

TABLE 2

| Strain | Amount of L-Threonine Accumulated (g/dl) |
|---|---|
| ATCC 13287 | 0.0 |
| SR 8301 | 0.15 |
| AJ 12168 | 0.63 |

EXAMPLE 2

Production of L-tryptophan in the presence of both the plasmid carrying tryptophan synthetase gene and the plasmid carrying shikimate kinase gene:

2-1. Cloning of shikimate kinase (SK) gene and 3-dehydroquinate synthetase (DOS) gene:

2-1-1. Preparation of donor DNA:

Chromosomal DNA was extracted from *Brevibacterium lactofermentum* AJ 11225 (FERM-P 4370) and purified, in the manner described in section 1-1-1.

2-1-2. Preparation of vector DNA:

To use pAJ 1844 (molecular weight, 5.4 megadaltons) as a vector, its DNA was prepared in the manner described in section 1-2-2.

2-1-3. Insertion of chromosomal DNA fragment into vector:

The chromosomal DNA, 10 μg, obtained in section 2-1-1 and 5 μg of the plasmid DNA obtained in section 2-1-2 were each treated with restriction endonuclease Pst I at 37° C. for 1 hour, to fully cleave the DNAs. After heating at 65° C. for 10 minutes, both reaction liquids were mixed with each other, and the mixture was subjected to a ligation reaction between the DNA strands with $T_4$ phage-derived DNA ligase at 10° C. for 24 hours in the presence of ATP and dithiothreitol. After heat treatment at 65° C. for 5 minutes, a 2-fold volume of ethanol was added to the reaction solution to harvest the ligated DNA precipitate.

2-1-4. Cloning of SK gene:

Shikimate kinase deficient *Brevibacterium lactofermentum* AJ 12157 was derived from *Brevibacterium lactofermentum* AJ 12036 (FERM-P 7559) by mutation with N-methyl-N-nitro-N-nitrosoguanidine selected as a mutant requiring 3 amino acids of phenylalanine, tryptophan and tyrosine for its growth. It was used as a recipient.

As a method for transformation, the protoplast transformation method described in section 1-1-4 was used. Incubation was conducted at 30° C. for 2 weeks on a regeneration medium containing 3 μg/ml of chloramphenicol. Approximately 25,000 colonies resistant to chloramphenicol appeared. They were replicated on a minimum medium and 5 strains having resistance to chloramphenicol and prototrophy of phenylalanine, tryptophan and tyrosine were obtained.

2-1-5. Plasmid analysis of the transformants:

To examine the hybrid plasmid a lysate was prepared by the method described in section 1-1-2. All of the five strains detected by agarose gel electrophoresis had plasmids obviously larger than vector pAJ 1844.

When the five plasmids were cleaved with restriction enzyme Pst I used for in vitro recombination, a DNA fragment of 2.9 kb. was noted. It was common to all of the plasmids. Accordingly, it is believed that SK gene is present on the 2.9 kb. fragment. The recombinant plasmid obtained by inserting the DNA fragment of 2.9 kb. at the cleavage site of vector pAJ 1844 with Pst I was named pAJ 927, and the strain carrying pAJ 927 was named AJ 12158 (FERM-P 7865).

2-1-6. Retransformation:

In order to confirm that the SK gene was present on the recombinant plasmid carrying the DNA fragment of 2.9 kb., *Brevibacterium lactofermentum* AJ 12157 was transformed using pAJ 927 DNA.

Among the colonies which appeared as chloramphenicol resistant, 10 strains were examined for their prototrophy for phenylalanine, tyrosine and tryptophan. All of the strains were prototroph and harbored plasmids similar in size to pAJ 927. It became clear that the SK gene was present on this plasmid.

2-1-7. Identification of 3-dehydroquinate synthetase on pAJ 927:

pAJ 927 was introduced into 3-dehydroquinate synthetase-deficient strain AB 2847 derived from *Escherichia coli* K-12 (J. Pittard et al., *J. Bacteriol.*, 1494, 91, 1966). pAJ 927 was introduced into AB 2847 by a method which increases the permeability of DNA by treating DNA recipient cells with calcium chloride.

Among colonies which appear as resistant to chloramphenicol, 10 strains were examined with respect to their prototrophy for phenylalanine, tyrosine and tryptophan. As a result, all of the colonies lost their auxotrophy for all three amino acids. Accordingly, it became clear that the SK gene and 3-dehydroquinate synthetase gene had been cloned on the inserted Pst I DNA fragment of 2.9 kb.

2-2. Transfer of the Pst I DNA fragment of 2.9 kb. carryinq the SK gene and the 3-dehydroquinate synthetase gene to vector plasmid pAJ 226

2-2-1. Formation of vector plasmid pAJ 228 having trimethoprim resistance:

(1) Chromosomal DNA was extracted from trimethoprim-resistant mutant AJ 12146 (FERM-P 7672) derived by mutation from *Brevibacterium lactofermentum* AJ 12036 and purified in the manner described in section 1-1-1.

(2) pAM 330 was used as a starting material. The DNA was prepared from *Brevibacterium lactofermentum* in the manner described in section 1-1-2.

(3) The chromosomal DNA (20 μg) obtained in (1) above and 10 μg of the plasmid DNA obtained in (2) above were each treated at 37° C. for 30 minutes with restriction endonuclease Mbo I. Both reaction liquids were mixed with each other, and the mixture was subjected to a ligation reaction.

(4) Trimethoprim-sensitive *Brevibacterium lactofermentum* AJ 12036 was used as a recipient. Transformation was accomplished by the method described in section 1-1-4. After culturing at 30° C. for 1 week on a regeneration medium containing 25 μg/ml of trimethoprim (Sigma Co.), approximately 100 colonies appeared. The colonies were replicated to a minimum medium containing 50 μg/ml of trimethoprim and one strain resistant to trimethoprim was obtained.

(5) When the plasmid DNA of this strain was examined by agarose gel electrophoresis, a plasmid obviously larger than vector pAM 330 was detected and named. The strain was named AJ 12147 (FERM-P 7673).

(6) In order to confirm that the trimethoprim-resistant gene was present on the plasmid (pAJ 228) carried on AJ 12147, *Brevibacterium lactofermentum* AJ 12036 was transformed using the plasmid DNA. Among the colonies which appear as trimethoprim-resistant, 10 strains were examined by agarose gel electrophoresis. It was found that the strains had plasmids of the same size as the size of pAJ 228. It thus became clear that the gene for expressing trimethoprim resistance was present on the recombinant plasmid pAJ 228.

2-2-2. Insertion of Pst I linker into pAJ 228:

pAJ 228 DNA (0.5 μg) was treated with restriction endonuclease Hpa I at 37° C. for 1 hour to fully cleave the DNA. After the treatment at 70° C. for 5 minutes, the reaction liquid was mixed with 1 μl (100 pmoles) of pPst I linker (Takara Shuzo Co.). The mixture was subjected to a ligation reaction between the DNA strands with $T_4$ phage-derived DNA ligase at 16° C. overnight in the presence of ATP and dithiothreitol. After heat treatment at 70° C. for 5 minutes, a 2-fold volume of ethanol was added to the reaction liquid to precipitate and harvest the DNA after completion of the ligation reaction. Using the DNA, *Brevibacterium lactofermentum* AJ 12036 was transformed. Then, from the trimethoprim-resistant colonies which appeared, 5 strains were selected at random, and from them a lystate was prepared and reacted with restriction endonuclease Pst I at 30° C. for 1 hour. DNA material obtained from each strain was subjected to 0.8% agarose gel electrophoresis and compared with Hind III fragments of λ phage having known weights (BRL Co.). By this procedure, a plasmid having a molecular weight of 5.1 Md, which was cleaved with Pst I at one site, was detected. This plasmid DNA was prepared in the manner described in section 1-1-2 and was reacted with various restriction endonucleases. The plasmid was not cleaved with Hpa I, but was cleaved with Pst I at one site. The plasmid exhibited the same cleavage as those of pAJ 228, when treated with other restriction endonucleases such as Bcl I, BstE II, Hae II, Hind III, Mlu I, and the like. From the foregoing results, it was confirmed that Pst I linker was inserted at the Hpa I cleavage site of pAJ 228. This plasmid wsa named pAJ 226.

2-2-3. Transfer of the 2.9 kb. Pst I DNA fragment of pAJ 927 to the Pst I site of pAJ 226:

pAJ 927 (5 μg) was fully cleaved with restriction enzyme Pst I, which has subjected to agarose gel electrophoresis. Pst I DNA fragment of 2.9 kb. was excised from the gel. After treatment with phenol and chloroform, a 2-fold volume of ethanol was added to recover the DNA as a precipitate. On the other hand, 2 μg of pAJ 226 was fully cleaved with the same enzyme. After heat treatment at 65° C. for 10 minutes, a 2-fold volume of ethanol was added to recover the DNA as a precipitate. Both DNAs recovered were dissolved in 20 μl of TEN buffer. After both solutions were mixed with each other, the mixture was subjected to a ligation reaction between the DNA strands with T4 phage-derived DNA ligase at 10° C. for 24 hours in the presence of ATP and dithiothreitol. After heat treatment at 65° C. for 5 minutes, a 2-fold volume of ethanol was added to the reaction liquid to harvest the ligated DNA precipitate. Then, using SK deficient *Brevibacterium lactofermentum* AJ 12157 as recipient, a transformation was performed by the transformation method used in section 1-1-4. After culturing at 30° C. for 10 days on regeneration medium containing 100 μg/ml of trimethoprim, the colonies which appeared were replicated on a minimal medium containing 50 μg/ml of trimethoprim to obtain strains showing prototrophy for phenylalanine, tyrosine and tryptophan. Plasmid DNA was detected in a representative of these strains. The pAJ 1120 plasmid obviously was larger than pAJ 226. pAJ 1220 DNA was cleaved with restriction enzyme Pst I used for the recombination, whereupon a DNA fragment of 2.9 kb. was detected, in addition to pAJ 226 of 7.6 kb.

2-3. Cloning of tryptophan synthease gene:

2-3-1. Preparation of chromosomal DNA carrying tryptophan synthetase (TS) gene:

Chromosomal DNA was extracted with *Brevibacterium lactofermentum* AJ 12030 (FERM-BP 276) which carries a TS gene which shows resistance to feedback inhibition by L-tryptophan and the DNA was purified in the manner described in section 1-1-1.

2-3-2. Preparation of vector DNA:

pAJ 1844 (molecular weight, 5.4 megadaltons) was used as vector and its DNA was purified using the method of section 1-1-2.

2-3-3. Insection of the chromosomal DNA fragment into vector:

The chromosomal DNA (20 μg) obtained in section 2-3-1 and 10 μg of the plasmid DNA obtained in section 2-3-2 were each treated with restricton endonuclease Pst I at 37° C. for 1 hour, to fully cleave the DNA. After the treatment at 65° C. for 10 minutes, both reaction liquids were mixed with each other, and the mixture was subjected to a ligation reaction between the DNA strands with T4 phage-derived DNA ligase at 10° C. for 24 hours in the presence of ATP and dithiothreitol. After heat treatment at 65° C. for 5 minutes, a 2-fold volume of ethanol was added to the reaction liquid to precipitate and harvest the DNA after completion of the ligation reaction.

2-3-4. Cloning of TS gene:

Using *Brevibacterium lactofermentum* No. 21 (a strain deficient in TS α subunits (hereafter simply referred to as TSA)) as a DNA recipient, 10 μg of the DNA prepared in section 2-3-3 was challenged by the method used in section 1-1-4. After culturing a 30° C. for 2 weeks on a regeneration medium containing 3 μg/ml of chloramphenicol, approximately 10,000 colonies appeared as chloramphenicol resistant. The colonies were replicated on a minimal medium and 3 strains having chloramphenicol resistance and having prototrophy for tryptophan were obtained.

2-3-5. Plasmid analysis of the transformant:

From the above three strains, lysates were prepared by the method described in section 1-1-2. When the plasmid DNA was examined by agarose gel electrophoresis, a transformant having a plasmid larger than vector pAJ 1844 was detected, and it was confirmed that the TSA gene was present on the recombinant plasmid carried by this strain. The strain was named AJ 12140 (FERM-P 7749) and the recombinant plasmid was named pAJ 319.

Further it became clear that the trp A gene, which codes a TS α subunit, and trp B gene, which codes a TSB subunit, were present on the 3.0 kb. fragment inserted at the Pst I site of pAJ 1844, since, when pAJ 319 was introduced into TS β subunit-(hereafter simply referred to as TSB)-deficient B-5 strain, the auxotrophy for tryptophan was lost.

2-4. Production of L-tryptophan in the presence of both pAJ 1220 and pAJ 319:

pAJ 1220 and pAJ 319 were transformed on a m-fluorophenylalanine- and 5-fluorotryptophan-resistant variant, *Brevibacterium lactofermentum* M 247, according to the method used in section 1-1-4.

After culturing at 30° C. for 10 days in a regeneration medium containing 3 μg/ml of chloramphenicol and 100 μg/ml of trimethoprim, colonies appeared, which were appropriately selected. The thus obtained strain showed resistance to both trimethoprim and chloramphenicol. Upon detection it was found that the strain had two kinds of plasmids, pAJ 319 and pAJ 1220. This strain AJ 12172 (FERM-P 7881) was cultured and examined for its L-tryptophan productivity. The results are shown in Table 3. Incubation was carried out by inoculating a medium at pH 6.5 containing 130 g of glucose, 25 g of $(NH_4)_2SO_4$, 12 g of fumaric acid, 3 g of acetic acid, 1 g of $KH_2PO_4$, 8 mg of $MnSO_4.4H_2O$, 1 g of $MgSO_4.7H_2O$, 50 μg of biotin, 2000 μg of thiamine hydrochloride, 650 mg of L-tyrosine, 400 mg of DL-methionine and 50 g of $CaCO_3$ in 1 liter of water with a specimen strain, either 3 ml of which had been separately charged in shoulder-equipped flasks. The cultures were agitated at 30° C. for 72 hours. After the incubation, L-tryptophan in the supernatant was quantitatively determined by micro-bioassay.

TABLE 3

| Strain | Amount of L-Tryptophan Accumulated (g/dl) |
|---|---|
| Brevibacterium lactofermentum M 247 | 0.16 |
| Brevibacterium lactofermentum AJ 12149 (M 247/pAJ 319) | 0.34 |
| Brevibacterium lactofermentum AJ 12172 (M 247/pAJ 319, pAJ 1220) | 0.58 | pAJ 319 and pAJ 1220 can be separated from deposited AJ 12172 in a conventional manner.

In order to obtain AJ 12061 and AJ 12157, it is possible to remove the composite plasmid from deposited AJ 12172, AJ 12066 and AJ 12157 without injury to the host cells. That is, the plasmid is spontaneously expelled from a host on occasion or it may also be removed by a specific plasmid removing operation (Bact. Rev., 36, 361–405 (1972)). An example of such a removing operation is as follows:

A CMG liquid medium is inoculated with AJ 12172. After culturing at 37° C. overnight, the culture solution is appropriately diluted. The dilution is spread on a CMG agar medium containing chloramphenicol and trimethoprim or a medium which is free of these materials by culturing at 30° C. for 1 to 3 days. The strains thus isolated as strains sensitive to chloramphenicol and trimethoprim are M 247, AJ 12066 and AJ 12157.

EXAMPLE 3

Production of L-threonine in the presence of a plasmid carrying homoserine dehydrogenase gene and a plasmid carrying homoserine kinase gene:

3-1. Cloning of homoserine kinase (HK) gene:

3-1-1. Preparation of chromosomal DNA carrying HK gene:

Chromosomal DNA was extracted from an α-amino-β-hydroxyvaleric acid (AHV)-resistant mutant AJ 11188 (FERM-P 4190) (Published Examined Japanese Patent Application No. 3038/81 of Brevibacterium lactofermentum ATCC 13869 and the DNA purified.

3-1-2. Preparation of vector DNA:

In order to use pAJ 1844 (molecular weight, 5.4 megadaltons) as a vector, its DNA was prepared in the manner described in section 1-1-2.

3-1-3. Insertion of chromosomal DNA fragment into vector:

The chromosomal DNA (20 μg), obtained in section 3-1-1 and 10 μg of the plasmid DNA obtained in section 3-1-2 were treated with restriction endonuclease Pst I at 37° C. for 1 hour, to fully cleave the DNA. After heat treatment at 65° C. for 10 minutes, both reaction liquids were mixed with each other, and the mixture was subjected to a ligation reaction between the DNA strands with T4 phage-derived DNA ligase at 10° C. for 24 hours in the presence of ATP and dithiothreitol. After heat tratment at 65° C. for 5 minutes, a 2-fold volume of ethanol was added to the reaction liquid to precipitate and harvest DNA after completion of the ligation reaction.

3-1-4. Cloning of HK gene:

HK deficient Brevibacterium lactofermentum AJ 12078 was used as a recipient. As a method for transformation, the protoplast transformation method described in section 1-1-4 was used. Using the DNA prepared in section 3-1-3, the protoplasts of AJ 12078 were transformed. After culturing at 30° C. for 2 weeks in a regeneration medium, approximately 10,000 colonies which appeared as chloramphenicol resistant were replicated on a minimal medium free of threonine, and 8 strains having chloramphenicol resistance and having protoropy for threonine were obtained.

3-1-5. Plasmid analysis of the transformant:

From these strains, a lysate was prepared by the method described in section 1-1-2. Agarose gel electrophoresis resulted in the detection of a plasmid obviously larger than vector pAJ 1844 and was named pAJ 211. This strain was named AJ 12079 (FERM-P 7237).

3-1-6. Retransformation:

In order to confirm that the HK gene was present on the recombinant plasmid (pAJ 211) in AJ 12079, Brevibacterium lactofermentum AJ 12078 was again transformed using the plasmid DNA.

From the chloramphenicol-resistant colonies which appeared, 10 strains were fished. An examination of auxotrophy for threonine revealed that all of the strains lost their auxotrophy, and it became clear that the HK gene was present on the recombinant plasmid described above.

3-2. Transfer of the 2.9 kb. Pst I DNA fragment carrying the HK gene to pAJ 224:

3-2-1. Transfer of the HK gene (2.9 kb. Pst I DNA fragment of pAJ 211) to trimethoprim-resistant plasmid (pAJ 228):

pAJ 228, prepared as described in section 2-2-1, had no cleavaqe sites with Pst I. It is thus impossible to transfer 211-derived Pst I fragment of 2.9 kb., which carries the HK gene, as it is. Therefore, transfer was carried out by the method shown in FIG. 1. That is, a synthetic oligonucleotide linker having cleavage sites with BamH I, Sal I and Pst I, as shown in FIG. 1, was ligated at the both terminals of the 2.9 kb. DNA fragment expelled from pAJ 211 by restriction Pst I using T4 phage-derived DNA ligase, followed by cleavage with restriction enzyme BamH I. The obtained DNA mixture was subjected to agarose gel electrophoresis to separate and extract a DNA fragment of about 2.9 kb. By precipitation with ethanol, the DNA fragment was recovered. The thus obtained DNA fragment has a structure in which the cleavage sites with Pst I, Sal I and BamH I form in line at both terminals of the DNA carrying the 2.9 kb HK genes (FIG. 1).

On the other hand, pAJ 228 was partially cleaved with restriction enzyme Mbo I followed by heat treatment at 65° C. for 10 minutes. The DNA fragment carrying the HK gene obtained in the manner described above was added to the reaction liquid to cause a ligation reaction between DNA strands with T4 ligase. After completion of the reaction, a heat treatment was carried out at 65° C. for 5 minutes. By the addition of a 2-fold volume of ethanol thereto, DNAs were precipitated and collected. The DNAs were subjected to protoplast transformation, using trimethoprim-sensitive and HK deficient Brevibacterium lactofermentum AJ 12078 as recipient in a manner similar to section 1-1-4. Thereafter, incubation was performed on a protoplast regeneration medium containing 100 μg/ml of trimethoprim. As a result, approximately 200 colonies were regenerated.

The colonies were replicated in a minimal medium containing 200 µg/ml of trimethoprim, but none of the threonine required by the recipient and 4 strains having trimethoprim resistance and the prototrophy for threonine was obtained. From these strains, a lysate was prepared by the method shown in section 1-1-2. When plasmid DNA was examined by agarose gel electrophoresis, plasmids of 14.9 kb, 12.2 kb, 9.6 kb and 6.5 kb were detected. Among the plasmids, the smallest plasmid of 6.5 kb was named pAJ 212. A strain carrying pAJ 212 was named 12078-HK.

pAJ 212, after the excision of the HK gene, has been deposited as pAJ 224 and as *Brevibacterium lactofermentum* AJ 12196 (FERM-P 8015).

3-2-2. Retransformation:

In order to confirm that the HK gene was present on the recombinant plasmid (pAJ 212) in AJ 12079, *Brevibacterium lactofermentum* AJ 12078 was transformed using the plasmid DNAs.

From the trimethoprim-resistant colonies which appeared, 10 strains were separated out. Examination of auxotrophy for threonine revealed that all of the strains lost auxotrophy and it became clear that the HK gene was present on the recombinant plasmid described above.

3-3. Production of L-threonine in the presence of both pAJ 210 and pAJ 212:

pAJ 210, carrying the homoserine dehydrogenase gene obtained in section 1-2 was introduced into a threonine-producing bacteria, AHV-resistant mutant, *Brevibacterium lactofermentum* AJ 11188 (FERM-P 4190), according to the transformation method used in section 1-1-4. A transformant was selected by chloramphenicol resistance, and to strain AJ 12021 (FERM-BP 270) was obtained.

In the same manner, pAJ 212 was introduced into the AJ 11188 strain and a transformant was selected by trimethoprim resistance and the 11188-HK strain was obtained.

Further, pAJ 212 was introduced into the AJ 12021 strain. A transformant was selected by chloramphenicol resistance and trimethoprim resistance and the strain AJ 12209 (FERM-P 8106), which carries two plasmids pAJ 210 and pAJ 212 was obtained.

AJ 11188, AJ 12021, 11188-HK and AJ 12209 strains were cultured (with shaking) at 30° C. for 72 hours in a threonine-producing medium (10 g/dl of glucose, 3 g/dl of $(NH_4)_2SO_4$, 0.1 g/dl of $KH_2PO_4$, 0.04 g/dl of $MgSO_4.7H_2O$, 10 mg of $FeSO_4.7H_2O$, 10 mg of $MnSO_4.5H_2O$, 300 µg/l of thiamine hydrochloride, 100 µg/l of biotin, 45 mg/l (as total nitrogen) of soybean protein acid hydrolysate ("Aji-Eki"), 25 mg/dl of isoleucine, 30 mg/dl of leucine, pH 7.0, 5 g/dl of $CaCO_3$ (separately sterilized). After the incubation, L-threonine, L-lysine and L-homoserine in the supernatant were each quantitatively determined by micro-bioassay or high speed liquid chromatography. The results are shown in Table 4.

pAJ 210 and pAJ 212 can be separated from deposited AJ 12209 in a conventional manner.

AJ 12019 can easily be obtained from AJ 12020, AJ 12078 from AJ 12079 or 12078-HK and AJ 11188 from AJ 12021, AJ 12080 or AJ 12209, by removing the composite plasmid in the host cells without injury to the host cells. The plasmid may be spontaneously expelled from a host on occasion or it may also be removed by a "removing" operation (*Bact. Rev.*, 36, 361–405 (1972)).

An example of a removing operation is as follows:

A medium containing acridine orange is inoculated with a small quantity of cells (approximately $10^4$/ml) in a concentration (2–50 mg/ml) that insufficiently inhibits the growth of a host bacteria. Then, incubation is conducted overnight at 27°–37° C. (*J. Bacteriol.*, 88, 261 (1964)). The culture solution is spread on an agar medium followed by incubation overnight at 27°–37° C. Among the colonies which appeared on the medium, strains sensitive to chloramphenicol (10 µg/ml) and trimethoprim (50 µg/ml), i.e., AJ 12019, AJ 12078 and AJ 11188, are strains from which plasmids are removed.

TABLE 4

| Strain | Amount of Each Amine Acid Accumulated (g/dl) | | |
|---|---|---|---|
| | L-Threonine | L-Lysine | L-Homoserine |
| AJ 11188 | 1.50 | 1.24 | 0.19 |
| AJ 12021 (AJ 11188/pAJ 210) | 2.20 | 0.26 | 0.70 |
| 11188-HK (AJ 11188/pAJ 212) | 2.10 | 0.43 | 0.11 |
| AJ 12209 (AJ 11188/pAJ 210, pAJ 212) | 3.36 | 0.12 | 0.18 |

Having now fully described this invention, it will be apparent to one of ordinary skill in the art that many changes and modifications can be made thereto without departing from the spirit or scope of the invention as set forth herein.

What is claimed as new and is intended to be secured by Letters Patent is:

1. A method for producing L-threonine, comprising culturing a microorganism of the genus Brevibacterium, wherein said microorganism contains the plasmids pAJ 210 and pAJ 201K.

2. A method for producing L-tryptophan, comprising culturing a microorganism of the genus Brevibacterium, wherein said microorganism contains the plasmids pAJ 1220 and pAJ 319.

3. A method for producing L-threonine, comprising culturing a microorganism of the genus Brevibacterium, wherein said microorganism contains the plasmids pAJ 212 and pAJ 210.

* * * * *